United States Patent
Jung

(10) Patent No.: US 8,450,515 B2
(45) Date of Patent: May 28, 2013

(54) PRODUCTION METHOD FOR LINEAR AND CYCLIC TRISILAALKANE

(75) Inventor: Il Nam Jung, Daejeon (KR)

(73) Assignee: Samsung Fine Chemicals Co., Ltd, Ulsan (KR)

( * ) Notice: Subject to any disclaimer, the term of this patent is extended or adjusted under 35 U.S.C. 154(b) by 105 days.

(21) Appl. No.: 12/994,818

(22) PCT Filed: May 22, 2009

(86) PCT No.: PCT/KR2009/002696
§ 371 (c)(1),
(2), (4) Date: Dec. 17, 2010

(87) PCT Pub. No.: WO2009/145523
PCT Pub. Date: Dec. 3, 2009

(65) Prior Publication Data
US 2011/0077420 A1    Mar. 31, 2011

(30) Foreign Application Priority Data

May 26, 2008    (KR) .................. 10-2008-0048681

(51) Int. Cl.
*C07F 7/08* (2006.01)
*C01B 33/107* (2006.01)

(52) U.S. Cl.
CPC .................................... *C01B 33/107* (2013.01)
USPC ............ 556/452; 556/409; 556/466; 556/467

(58) Field of Classification Search
USPC .................. 556/406, 409, 452, 465, 466, 467
See application file for complete search history.

(56) References Cited

U.S. PATENT DOCUMENTS

| | | | | |
|---|---|---|---|---|
| 2,381,000 A | * | 8/1945 | Patnode et al. | 556/435 |
| 5,998,649 A | * | 12/1999 | Jung et al. | 556/406 |
| 6,392,077 B1 | * | 5/2002 | Jung et al. | 556/481 |

OTHER PUBLICATIONS

Jung, E.D. et al, Journal of Organometallic Chemistry 692 (2007) 3901-3906.*
Kang, S. et al, Organometallics 2006, 25, 318-319.*
Phan, S.T. et al, Organometallics 2004, 23, 169-171.*
Shimojima A. et al, Chemical Communications 2004, 2672-2673.*
Phan, S.T. et al, Journal of Organometallic Chemistry 691 (2006) 604-610.*

* cited by examiner

*Primary Examiner* — Johann R Richter
*Assistant Examiner* — Pancham Bakshi
(74) *Attorney, Agent, or Firm* — Lowe Hauptman Ham & Berner, LLP

(57) ABSTRACT

The present invention relates to a preparation method for a linear or cyclic trisilaalkane which is a substance useful in the preparation of polycarbosilane and silicon carbide precursors. Linear or cyclic trisilaalkane and organic trichlorosilane derivatives can be synthesized simultaneously and in high yield by reacting bis(chlorosily)methane having a Si—H bond, either alone or together with an organic chloride, using a quaternary organic phosphonium salt compound as a catalyst. Further, since the catalyst can be recovered after use, the present invention is very economical and is thus effective for mass-producing precursors for organic/inorganic hybrid substances.

9 Claims, No Drawings

PRODUCTION METHOD FOR LINEAR AND CYCLIC TRISILAALKANE

BACKGROUND OF THE INVENTION

1. Field of the Invention

The present invention relates to a preparation method for linear or cyclic trisilaalkane and, more particularly, to a method for obtaining linear or cyclic trisilaalkane by reacting bis(chlorosily)methane having a Si—H bond alone or simultaneously preparing organic trichlorosilane derivatives by reacting bis(chlorosily)methane having a Si—H bond together with an organic chloride, b using a quaternary organic phosphonium salt compound as a catalyst.

2. Description of the Related Art

Recently, the inventors of the present application have reported a method in which alkylchloride having a C—Cl bond and a trichlorosilane (HSiCl$_3$) having an Si—H bond were reacted by using a tetraalkyl phosphonium chloride compound as a catalyst to form a silicon-carbon (Si—C) bond, while removing hydrogen chloride upon producing it by detaching chlorine from alkylchloride and hydrogen from the trichlorosilane (HSiCl$_3$), to thus synthesize various organic silicon compounds (Y. S. Cho; S-H. Kang; J. S. Han; B. R. Yoo; II Nam Jung; J. Am. Chem. Soc., 123, 2001, 5583; I. N. Jung et al, U.S. Pat. No. 6,392,077). This dehydrochlorination is a novel method for forming a silicon-carbon bond, which is very useful for synthesizing various novel organic silicon compounds.

As the organic chloride such as alkychloride, an alkylchloride that does not have a strong activity, cyclic alkyl chloride, and tertiary alkyl chloride, as well as alkylchloride in which chlorine is bonded to carbon having a strong activity, such as benzyl chloride or allyl chloride, may be reacted to synthesize an organic silicon chloride with a high yield. In addition, it has been known that methyldichlorosilane (MeHSiCl$_2$), instead of trichlorosilane (HSiCl$_3$), can be used to cause a reaction of forming silicon-carbon (Si—C) bond although a yield is lowered.

It has been also reported that when it is applied, instead of alkylchloride, to alkene with a carbon-carbon double bond by using a tetraalkyl phosphonium chloride compound as a catalyst, double silylation in which trichlorosilyl group is included in carbons of both sides of the double bond takes place. It has been known that this is because a dichlorosilylene (SiCl$_2$) intermediate created by detaching hydrogen chloride from trichlorosilane (HSiCl$_3$) is added to the carbon-carbon double bond in the reaction path of the reaction.

Meanwhile, the inventors of the present application have noticed that when various organic compounds having a chloromethyl group are mixed with hydrogen chloride and reacted with metal silicon, a bissilylmethane having an Si—H bond and two silanes substituting one carbon. Also, when methylene chloride and hydrogen chloride having two carbon-chlorine bonds are mixed and reacted with silicon by using a copper catalyst, bis(dichlorosilyl)methane and (dichlorosilyl)(trichlorosilyl)methane are obtained.

Meanwhile, conventionally, it has been reported that, in preparing a cyclic organic silicon compound such as 1,3-disilacyclobutane, when dichlorosilacyclobutane is thermally decomposed at a high temperature of 690° C., dichlorosylene (CH$_2$=SiCl$_2$), an intermediate, is created, and when dichlorosylene is dimerized, 1,1,3,3-tetrachloro-1,3-disilacyclobutane is created (N. Auner and J. Grobe, J. Organometal. Chem. 1980, 188, 151; 200, 129). However, in order to prepare dichlorosilacyclobutane, a raw material, the Grignard method must be employed and the reaction of thermal decomposition at a high temperature generally does not have a good yield.

Also, it has been reported that when methylchloride is reacted with metal silicon through a direct method, 1,1,3,3,5,5-hexachloro-1,3,5-trisilacyclohexane is obtained as a by-product. However, the reaction between methylene chloride and metal silicon is not in use because of a problem in that the activity of metal silicon and a copper catalyst are drastically degraded due to carbon generated as methylene chloride is decomposed at a high reaction temperature of 300° C., and a problem in that the activity of reactants are degraded due to polymer carbosilane generated as methylene chloride and metal silicon are reacted.

SUMMARY OF THE INVENTION

Therefore, the inventors of the present application intend to solve the is related art problems in preparing a linear or cyclic trisilaalkane, a precursor useful for producing polycarbosilane or an organic or inorganic hybrid material with a high efficiency.

An object of the present invention is to provide a method for preparing linear and cyclic trisilaalkane compounds.

According to embodiments of the present invention, linear or cyclic trisilaalkane, a precursor useful for producing polycarbosilane or an organic or inorganic hybrid material, can be synthesized simultaneously through a novel synthesizing method with a high yield by reacting bis(chlorosily)methane having a Si—H bond alone or together with an organic chloride by using a quaternary organic phosphonium salt compound as a catalyst. Further, because the catalyst can be recovered after its use, the present invention is very economical and thus effective for mass-producing precursors for organic/inorganic hybrid substances.

To achieve the above object, there is provided method for preparing a cyclic trisilaalkane represented by Chemical Formula 2 or a linear trisilaalkane represented by Chemical Formula 3 by reacting bischlorosilylmethane having an Si—H bond represented by Chemical Formula 1 shown below alone under the presence of a quaternary organic phosphonium salt catalyst.

[Chemical Formula 1]

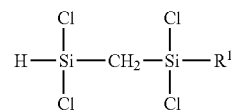

In Chemical Formula 1, R1 is hydrogen, a halogen atom, or an alkyl group.

[Chemical Formula 2]

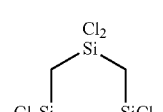

[Chemical Formula 3]

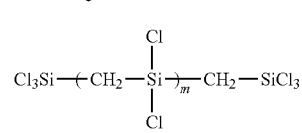

In Chemical Formula 3, m is 0 or 1.

DETAILED DESCRIPTION OF THE INVENTION

The present invention will now be described in detail as follows.

Cyclic and linear trisilaalkanes according to an embodiment of the present invention are represented by Chemical Formula 2 and Chemical Formula 3 as shown above, respectively, and can be obtained by reacting bischlorosilylmethane represented by Chemical Formula 1 under the presence of a quaternary organic phosphonium salt catalyst.

The bischlorosilylmethane compound represented by Chemical Formula 1 may be, for example, one selected from the group consisting of (dichlorosilylmethyl)dichlorosilane, (trichlorosilylmethyl)dichlorosilane, (chloromethyl)methyldichlorosilane, and (methyldichlorosilylmethyl)dichlorosilane. The biischlorosilylmethane may have a Si—H bond and two or more chlorosilyl groups. A cyclic or linear trisilaalkane may be prepared by reacting bischlorosilylmethane alone.

The quaternary organic phosphonium salt as a catalyst used for preparing the cyclic or linear trisilaalkane may be represented by Chemical Formula 4a or 4b shown below:

[Chemical Formula 4a]

[Chemical Formula 4b]

In Chemical Formulas 4a and 4b, X is a halogen atom, $R^3$, which is the same or different, indicates an alkyl group of $C_1$~$C_{12}$ or —$(CH_2)_n$-$C_6H_5$ (here, n is 0 or 1~6), two R3s can be covalently bonded to form 4-atom rings or 8-atom rings, and Y is an alkylene group of $C_1$~$C_{12}$.

Preferably, the quaternary organic phosphonium salt catalyst is used within the range of 0.05 mol to 0.5 mol with respect to 1 mol of bischlorosilylmethane having the Si—H bond represented by Chemical Formula 1.

Meanwhile, as the quaternary organic phosphonium salt catalyst according to the present invention, the quaternary organic phosphonium salt compound represented by Chemical Formula 4a or 4b may be directly used, or a catalyst immobilized in one or more carriers selected from the group constituting of a silicon resin, silica, inorganic complexing agent, and an organic polymer. For example, the silicon resin has a structure including phosphonium salts having a catalyst activity for the silicon resin, like the structure of $(Cl^-Bu_3P^+(CH_2)_3$—$SiO_{3/2})_n$, and the other carriers have a structure in which phosphonium salts having a catalyst activity is immobilized in the carriers, similarly.

The technique of immobilizing the catalyst in various carriers is not particularly limited but follows the general catalyst immobilization method, and a detailed description thereof will be omitted.

Preferably, the reaction according to an exemplary embodiment of the is present invention is performed within a temperature range of 10° C. to 250° C. Also, preferably, the reaction is performed without a reaction solvent, and selectively, it may be performed as necessary under the presence of an aromatic hydrocarbon solvent of one or more selected from the group consisting of benzene, toluene, and xylene.

When the bischlorosilylmethane having the Si—H bond represented by Chemical Formula 1 is reacted along under the presence of a catalyst, the cyclic trisilaalkane represented by Chemical Formula 2 and the linear trisilaalkane represented by Chemical Formula 3 can be obtained together.

Meanwhile, when the organic chloride represented by Chemical Formula 5 shown below is selectively reacted together in the event of the above reaction, an organic trichlorosilane derivative represented by Chemical Formula 6 can be simultaneously obtained, besides the cyclic trisilaalkane represented by Chemical Formula 2 and the linear trisilaalkane represented by Chemical Formula 3.

[Chemical Formula 5]

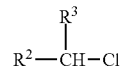

In Chemical Formula 5, $R^2$ is selected from among a halogen atom; a linear or cyclic alkyl group having 1 to 6 carbons; a silane derivative residue selected from the group consisting of —$SiCl_3$, —$SiMeCl_2$, —$SiHCl_2$, —$SiMe_2Cl$, and —$SiMe_3$; an alkene group having 2 to 5 carbons containing an unsaturated bond; an aromatic group represented as —Ar(R')q (here, Ar is aromatic hydrocarbon having 6 to 14 carbons, R' is an alkyl group, halogen, an alkoxy group, or a vinyl group, each having 1 to 4 carbons, and q is an integer of 0 to 5); an alkyl chloride group represented as —$(CH_2)_pCl$ (here, p is an integer of 1 to 9); or methyl chloride aromatic group represented as —$Ar(CH_2)Cl$ (here, Ar is aromatic group hydrocarbon having 6 to 14 carbons), and $R^3$ is selected from among a hydrogen atom; a halogen atom; a linear or cyclic alkyl group having 1 to 6 carbons; and an aromatic group represented as —Ar(R')q (here, Ar is aromatic hydrocarbon having 6 to 14 carbons, R' is an alkyl group, halogen, an alkoxy group, or a vinyl group, each having 1 to 4 carbons, and q is an integer of 0 to 5).

The organic chloride represented by Chemical Formula 5 may be primary or secondary alkyl chloride in which aliphatic and an aromatic organic groups are substituted, a silyl group-substituted methylchloride, and the like, but not limited thereto.

[Chemical Formula 6]

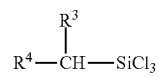

In Chemical Formula 6, $R^3$ is selected from among a hydrogen atom; a linear or cyclic alkyl group having 1 to 6 carbons; or an aromatic group represented as —Ar(R')q (here, Ar is aromatic hydrocarbon having 6 to 14 carbons, R' is an alkyl group, halogen, an alkoxy group, or a vinyl group, each having 1 to 4 carbons, and q is an integer of 0 to 5), and $R^4$ is selected from among a linear or cyclic alkyl group having 1 to 6 carbons; a silane derivative residue selected from the group consisting of —$SiCl_3$, —$SiMeCl_2$, —$SiHCl_2$, —$SiMe_2Cl$, and —$SiMe_3$; an alkene group having 2 to 5 carbons containing an unsaturated bond; or an aromatic group represented as —Ar(R')q (here, Ar is aromatic hydrocarbon having 6 to 14 carbons, R' is an alkyl group, halogen, an alkoxy group, or a vinyl group, each having 1 to 4 carbons, and q is an integer of 0 to 5), wherein when $R^2$ in Chemical Formula 5 is —$(CH_2)pCl$, —$Ar(CH_2)Cl$, $R^4$ in Chemical Formula 6 is —$(CH_2)pSiCl_3$, —$Ar(CH_2)SiCl_3$.

When bischlorosilylmethans having the Si—H bond represented by Chemical Formula 1 and having two or more chlorosilyl groups are reacted by using the quaternary organic phosphonium salt compound as a catalyst, the cyclic trisilaalkane represented by Chemical Formula 2 or the linear trisilaalkane represented by Chemical Formula 3 are obtained, and when the organic chloride having the C—Cl bond represented by Chemical Formula 5 is additionally reacted together in the event of the reaction, the organic trichlorosilane derivative represented by Chemical Formula 6 can be simultaneously synthesized besides the cyclic or linear trisilaalkane.

In this reaction, the organic trichlorosilane derivative represented by Chemical Formula 6 is generated as trichlorosilane, which is generated as bischlorosilylmethane represented by Chemical Formula 1 is decomposed, is reacted with alkylchloride.

Namely, as bischlorosilylmethane is decomposed, trichlorosilane is generated, and the other remaining generates dichlorosylene ($CH_2=SiCl_2$). This dichlorosylene is a highly reactive intermediate, so with a compound causing a nucleophilic reaction such as alcohol, amine, trimethylmethoxysilane, and the like, dichlorosylene is easily reacted therewith, and without the nucleophilic reactant, dichlorosylene is dimerized to form 1,1,3,3-tetrachloro-1,3-disilacyclobutane.

However, in an exemplary embodiment of the present invention, 1,3-disilacyclobutane, a dimerization product of dichlorosylene generated as bischlorosilylmethane is decomposed, was not obtained, but linear or cyclic trisilaalkanes were produced.

This is estimated such that 1 mol of dichlorosylene ($CH_2=SiCl_2$) is added to 1,3-disilacyclobutane in a reaction condition as shown in the following Reactive Formula 1 to form 1,1,3,3,5,5-hexachloro-1,3,5-trisilacyclohexane or form linear 1,3,5-trisilapentane with trichlorosilane according to ring opening.

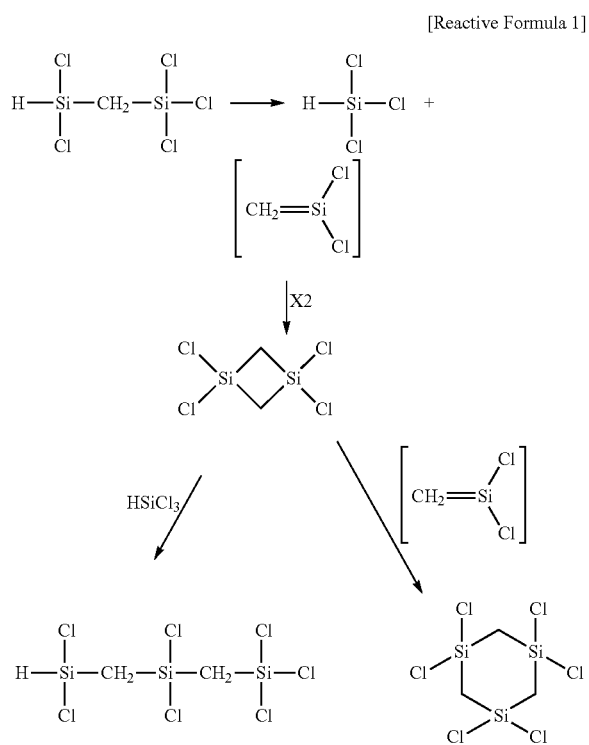

[Reactive Formula 1]

Meanwhile, in the present invention, preferably, the organic chloride represented by Chemical Formula 5 is reacted within the range of 0.5 mol to 8 mol with respect to 1 mol of bischlorosilylmethane having the Si—H bond represented by Chemical Formula 1.

In the present invention, when bischlorosilylmethane represented by Chemical Formula 1 is reacted along by using the quaternary organic phosphonium salt compound catalyst, the linear or cyclic organic silane to compounds can be obtained, while trichlorosilane additionally produced from the reaction causes ring opening of the cyclic organic silane compound, lowering the yield of the cyclic organic silane compound.

Thus, when the organic chloride represented by Chemical Formula 5 which reacts with trichlorosilane is reacted together, the formation of the linear trisilapentane can be restraining, and thus, the cyclic organic silane compound of a high yield can be obtained.

The following embodiments will specify the present invention, but the scope of the present invention is not limited thereto.

Embodiment 1: Reaction of (trichlorosilylmethyl)dichlorosilane (catalyst: tetrabutylphosphonium chloride)

A reaction vessel formed as a 25 ml stainless steel tube dried in an oven was cooled under the presence of a dried nitrogen gas, in which 12.4 g (0.050 mol) of (trichlorosilylmethyl)dichlorosilane and 1.5 g (0.005 mol) of tetrabutylphosphonium chloride were then put. The entrance of the reaction vessel was hermetically sealed with a stopper, reaction was performed at 180° C. for three hours, and then, a consumption of a starter and a product were checked through a gas chromatography. 2.8 g (yield: 49.6%) of 1,1,3,3,5,5-hexachloro-1,3,5-trisilacyclohexane and 1.4 g (yield: 14.1%) of 1,1,1,3,3,5,5,5-octachloro-1,3,5-trisilapentane were obtained through vacuum distillation of a reactant.

The results of analyzing the obtained products by using 300 MHz 1H magnetic resonance showed that, in 1,1,3,3,5, 5-hexachloro-1,3,5-trisilacyclohexane, Si—$CH_2$—Si peak was confirmed at δ1.46 ppm (s, 6H), and in 1,1,1,3,3,5,5,5-octachloro-1,3,5-trisilapentane, Si—$CH_2$—C peak was confirmed at δ1.71 ppm (s, 4H).

Embodiment 2: Reaction of (trichlorosilylmethyl)dichlorosilane (catalyst: tetraethylphosphonium chloride)

In the same manner as that of Embodiment 1, 12.4 g (0.005 mol) of (trichlorosilylmethyl)dichlorosilane and 0.9 g (0.005 mol) of tetraethylphosphonium chloride were put in a 25 ml stainless steel tube and reacted at 180° C. for three hours. The reactant was vacuum-distilled to obtain 2.5 g (yield: 44.2%) of 1,1,3,3,5,5-hexachloro-1,3,5-trisilacyclohexane and 1.1 g (yield: 11.1%) of 1,1,1,3,3,5,5,5-octachloro-1,3,5-trisilapentane were obtained.

The results of analyzing the obtained products by using 300 MHz 1H magnetic resonance showed that, in 1,1,3,3,5, 5-hexachloro-1,3,5-trisilacyclohexane, Si—$CH_2$—Si peak was confirmed at δ1.46 ppm (s, 6H), and in 1,1,1,3,3,5,5,5-octachloro-1,3,5-trisilapentane, Si—$CH_2$—C peak was confirmed at δ1.71 ppm (s, 4H).

Embodiment 3: Reaction of benzylchloride and (trichlorosilylmethyl)dichlorosilane (catalyst: tetrabutylphosphonium chloride)

In the same manner as that of Embodiment 1, 3.8 g (0.030 mol) of benzylchloride, 7.5 g (0.030 mol) of (trichlorosilylmethyl)dichlorosilane, and 0.9 g (0.003 mol) of tetrabutylphosphonium chloride were put in a 25 ml stainless steel tube and reacted at 130° C. for two hours. The reactant was vacuum-distilled to obtain 1.2 g (yield: 35.4%) of 1,1,3,3,5, 5-hexachloro-1,3,5-trisilacyclohexane, 0.9 g (yield: 15.2%) of 1,1,1,3,3,5,5,5-octachloro-1,3,5-trisilapentane, and 0.7 g (yield: 10.3%) of benzytrichloro silane were obtained.

The results of analyzing the obtained products by using 300 MHz 1H magnetic resonance showed that, in benzyltrichloro silane, Si—$CH_2$—C peak was confirmed at δ2.92 ppm (s, 2H), and Ar—H peak was confirmed at δ7.31 ppm (m, 5H). In 1,1,3,3,5,5-hexachloro-1,3,5-trisilacyclohexane, Si—$CH_2$—Si peak was confirmed at δ1.46 ppm (s, 6H). In 1,1,1,3,3,5,5,5-octachloro-1,3,5-trisilapentane, Si—CH$_2$—C peak was confirmed at δ1.71 ppm (s, 4H).

Embodiment 4: Reaction of benzylchloride and (trichlorosilylmethyl)dichlorosilane (catalyst: tetraphenylphosphonium chloride Fw 374.84)

In the same manner as that of Embodiment 1, 3.8 g (0.030 mol) of benzylchloride, 7.5 g (0.030 mol) of (trichlorosilylmethyl)dichlorosilane, and 1.1 g (0.003 mol) of tetraphenylphosphonium chloride were put in a 25 ml stainless steel tube and reacted at 180° C. for six hours. The reactant was vacuum-distilled to obtain 1.3 g (yield: 38.3%) of 1,1,3,3,5,5-hexachloro-1,3,5-trisilacyclohexane, 1.0 g (yield: 16.8%) of 1,1,1,3,3,5,5,5-octachloro-1,3,5-trisilapentane, and 0.7 g (yield: 10.3%) of benzytrichloro silane were obtained.

The results of analyzing the obtained products by using 300 MHz 1H magnetic resonance showed that, in benzyltrichloro silane, Si—CH$_2$—C peak was confirmed at δ2.92 ppm (s, 2H), and Ar—H peak was confirmed at δ7.31 ppm (m, 5H). In 1,1,3,3,5,5-hexachloro-1,3,5-trisilacyclohexane, Si—CH$_2$—Si peak was confirmed at δ1.46 ppm (s, 6H). In 1,1,1,3,3,5,5,5-octachloro-1,3,5-trisilapentane, Si—CH$_2$—C peak was confirmed at δ1.71 ppm (s, 4H).

Embodiment 5: Reaction of methylene chloride and (trichlorosilylmethyl)dichlorosilane (catalyst: tetrabutylphosphonium chloride)

In the same manner as that of Embodiment 1, 2.2 g (0.026 mol) of methylene chloride, 12.4 g (0.050 mol) of (trichlorosilylmethyl)dichlorosilane, and 1.5 g (0.005 mol) of tetrabutylphosphonium chloride were put in a 25 ml stainless steel tube and reacted at 180° C. for two hours. The reactant was vacuum-distilled to obtain 3.7 g (yield: 65.5%) of 1,1,3,3,5,5-hexachloro-1,3,5-trisilacyclohexane, 1.4 g (yield: 14.1%) of 1,1,1,3,3,5,5,5-octachloro-1,3,5-trisilapentane, and 3.3 g (yield: 44.8%) of bis(trichlorosilyl)methane were obtained.

The results of analyzing the obtained products by using 300 MHz 1H magnetic resonance showed that, in bis(trichlorosilyl)methane, Si—CH$_2$—Si peak was confirmed at δ1.86 ppm (s, 2H). In 1,1,3,3,5,5-hexachloro-1,3,5-trisilacyclohexane, Si—CH$_2$—Si peak was confirmed at δ1.46 ppm (s, 6H). In 1,1,1,3,3,5,5,5-octachloro-1,3,5-trisilapentane, Si—CH$_2$—C peak was confirmed at δ1.71 ppm (s, 4H).

Embodiment 6: Reaction of methylene chloride and (trichlorosilylmethyl)dichlorosilane (catalyst: benzyltriphenylphosphonium chloride)

In the same manner as that of Embodiment 1, 2.2 g (0.026 mol) of methylene chloride, 12.4 g (0.050 mol) of (trichlorosilylmethyl)dichlorosilane, and to 1.9 g (0.005 mol) of benzyltriphenylphosphonium chloride were put in a 25 ml stainless steel tube and reacted at 180° C. for three hours. The reactant was vacuum-distilled to obtain 3.5 g (yield: 61.9%) of 1,1,3,3,5,5-hexachloro-1,3,5-trisilacyclohexane, 1.2 g (yield: 12.1%) of 1,1,1,3,3,5,5,5-octachloro-1,3,5-trisilapentane, and 2.8 g (yield: 38.0%) of bis(trichlorosilyl)methane were obtained.

The results of analyzing the obtained products by using 300 MHz 1H magnetic resonance showed that, in bis(trichlorosilyl)methane, Si—CH$_2$—Si peak was confirmed at δ1.86 ppm (s, 2H). In 1,1,3,3,5,5-hexachloro-1,3,5-trisilacyclohexane, Si—CH$_2$—Si peak was confirmed at δ1.46 ppm (s, 6H). In 1,1,1,3,3,5,5,5-octachloro-1,3,5-trisilapentane, Si—CH$_2$—C peak was confirmed at δ1.71 ppm (s, 4H).

Embodiment 7: Reaction of (dichlorosilylmethyl)dichlorosilane (catalyst: tetrabutylphosphonium chloride)

In the same manner as that of Embodiment 1, 6.8 g (0.032 mol) of (dichlorosilylmethyl)dichlorosilane and 0.9 g (0.003 mol) of tetrabutylphosphonium chloride were put in a 25 ml stainless steel tube and reacted at 180° C. for three hours. The reactant was vacuum-distilled to obtain 1.4 g (yield: 38.7%) of 1,1,3,3,5,5-hexachloro-1,3,5-trisilacyclohexane and 0.1 g (yield: 1.6%) of 1,1,1,3,3,5,5,5-octachloro-1,3,5-trisilapentane were obtained.

The results of analyzing the obtained products by using 300 MHz 1H magnetic resonance showed that, in 1,1,3,3,5,5-hexachloro-1,3,5-trisilacyclohexane, Si—CH$_2$—Si peak was confirmed at δ1.46 ppm (s, 6H). In 1,1,1,3,3,5,5,5-octachloro-1,3,5-trisilapentane, Si—CH$_2$—C peak was confirmed at δ1.71 ppm (s, 4H).

Embodiment 8: Reaction of (dichlorosilylmethyl)dichlorosilane (catalyst: benzyltributylphosphonium chloride)

In the same manner as that of Embodiment 1, 6.8 g (0.032 mol) of (dichlorosilylmethyl)dichlorosilane and 1.0 g (0.003 mol) of benzyltributylphosphonium chloride were put in a 25 ml stainless steel tube and reacted at 180° C. for four hours. The reactant was vacuum-distilled to obtain 1.4 g (yield: 38.7%) of 1,1,3,3,5,5-hexachloro-1,3,5-trisilacyclohexane and 0.1 g (yield: 1.6%) of 1,1,1,3,3,5,5,5-octachloro-1,3,5-trisilapentane were obtained.

The results of analyzing the obtained products by using 300 MHz 1H magnetic resonance showed that, in 1,1,3,3,5,5-hexachloro-1,3,5-trisilacyclohexane, Si—CH$_2$—Si peak was confirmed at δ1.46 ppm (s, 6H). In 1,1,1,3,3,5,5,5-octachloro-1,3,5-trisilapentane, Si—CH$_2$—C peak was confirmed at δ1.71 ppm (s, 4H).

Embodiment 9: Reaction of benzylchloride and (dichlorosilylmethyl)dichlorosilane (catalyst: tetrabutylphosphonium chloride)

In the same manner as that of Embodiment 1, 3.8 g (0.030 mol) of benzylchloride, 7.5 g (0.035 mol) of (dichlorosilylmethyl)dichlorosilane and 0.9 g (0.003 mol) of tetrabutylphosphonium chloride were put in a 25 ml stainless steel tube and reacted at 180° C. for three hours. The reactant was vacuum-distilled to obtain 0.9 g (yield: 27.8%) of 1,1,3,3,5,5-hexachloro-1,3,5-trisilacyclohexane, 0.3 g (yield: 4.6%) of 1,1,1,3,3,5,5,5-octachloro-1,3,5-trisilapentane, and 2.8 g (yield: 41.7%) of benzytrichloro silane were obtained.

The results of analyzing the obtained products by using 300 MHz 1H magnetic resonance showed that, in benzyltrichloro silane, Si—CH$_2$—C peak was confirmed at δ2.92 ppm (s, 2H), and Ar—H peak was confirmed at δ7.31 ppm (m, 5H). In 1,1,3,3,5,5-hexachloro-1,3,5-trisilacyclohexane, Si—CH$_2$—Si peak was confirmed at δ1.46 ppm (s, 6H). In 1,1,1,3,3,5,5,5-octachloro-1,3,5-trisilapentane, Si—CH$_2$—C peak was confirmed at δ1.71 ppm (s, 4H).

Embodiment 10: Reaction of benzylchloride and (dichlorosilylmethyl)dichlorosilane (catalyst: catalyst obtained by immobilizing {3-(tributylphosphonium)propyl}chloride in silicon resin carrier)

In the same manner as that of Embodiment 1, 3.8 g (0.030 mol) of benzylchloride, 7.5 g (0.035 mol) of (dichlorosilylmethyl)dichlorosilane and 1.5 g of silicon resin [(RSiO$_{3/2}$)n, R={3-(tributylphosphonium)propyl}chloride] were put in a 25 ml stainless steel tube and reacted at 180° C. for twelve hours. The reactant was vacuum-distilled to obtain 0.9 g (yield: 25.5%) of 1,1,3,3,5,5-hexachloro-1,3,5-trisilacyclohexane, 0.2 g (yield: 4.0%) of 1,1,1,3,3,5,5,5-octachloro-1,3,5-trisilapentane, and 2.7 g (yield: 39.3%) of benzytrichloro silane were obtained.

The results of analyzing the obtained products by using 300 MHz 1H magnetic resonance showed that, in benzyltrichloro silane, Si—CH$_2$—C peak was confirmed at δ2.92 ppm (s, 2H), and Ar—H peak was confirmed at δ7.31 ppm (m, 5H). In 1,1,3,3,5,5-hexachloro-1,3,5-trisilacyclohexane, Si—CH$_2$—Si peak was confirmed at δ1.46 ppm (s, 6H). In 1,1,1,3,3,5,5,5-octachloro-1,3,5-trisilapentane, Si—$CH_2$—C peak was confirmed at δ1.71 ppm (s, 4H).

Embodiment 11: Reaction of methylene chloride and (dichlorosilylmethyl)dichlorosilane (catalyst: tetrabutylphosphonium chloride)

In the same manner as that of Embodiment 1, 2.0 g (0.024 mol) of methylene chloride, 8.6 g (0.040 mol) of (dichlorosilylmethyl)dichlorosilane, and 1.2 g (0.004 mol) of tetrabutylphosphonium chloride were put in a 25 ml stainless steel tube and reacted at 180° C. for two hours. The reactant was vacuum-distilled to obtain 3.2 g (yield: 70.1%) of 1,1,3,3,5,5-hexachloro-1,3,5-trisilacyclohexane, 1.0 g (yield: 13.0%) of 1,1,1,3,3,5,5,5-octachloro-1,3,5-trisilapentane, and 2.3 g (yield: 40.6%) of bis(trichlorosilyl) were obtained.

The results of analyzing the obtained products by using 300 MHz 1H magnetic resonance showed that, in bis(trichlorosilyl), Si—$CH_2$—C peak was confirmed at δ1.86 ppm (s, 2H). In 1,1,3,3,5,5-hexachloro-1,3,5-trisilacyclohexane, Si—$CH_2$—Si peak was confirmed at δ1.46 ppm (s, 6H). In 1,1,1,3,3,5,5,5-octachloro-1,3,5-trisilapentane, Si—$CH_2$—C peak was confirmed at δ1.71 ppm (s, 4H).

Embodiment 12: Reaction of (methyldichlorosilylmethyl)dichlorosilane (catalyst: tetrabutylphosphonium chloride)

In the same manner as that of Embodiment 1, 11.4 g (0.043 mol) of (methyldichlorosilylmethyl)dichlorosilane and 1.26 g (0.004 mol) of tetrabutylphosphonium chloride were put in a 25 ml stainless steel tube and reacted at 180° C. for three hours. The reactant was vacuum-distilled to obtain 1.56 g (yield: 32.0%) of 1,1,3,3,5,5-hexachloro-1,3,5-trisilacyclohexane and 0.5 g (yield: 6.0%) of 1,1,1,3,3,5,5,5-octachloro-1,3,5-trisilapentane were obtained.

The results of analyzing the obtained products by using 300 MHz 1H magnetic resonance showed that, in 1,1,3,3,5,5-hexachloro-1,3,5-trisilacyclohexane, Si—$CH_2$—Si peak was confirmed at δ1.46 ppm (s, 6H). In 1,1,1,3,3,5,5,5-octachloro-1,3,5-trisilapentane, Si—$CH_2$—C peak was confirmed at δ1.71 ppm (s, 4H).

Embodiment 13: Reaction of 1-chloro hexane and (trichlorosilylmethyl)dichlorosilane (catalyst: tetrabutylphosphonium chloride)

In the same manner as that of Embodiment 1, 3.8 g (0.032 mol) of 1-chloro hexane and 7.5 g (0.030 mol) of (trichlorosilylmethyl)dichlorosilane, and 0.9 g (0.003 mol) of tetrabutylphosphonium chloride were put in a 25 ml stainless steel tube and reacted at 170° C. for two hours. The reactant was vacuum-distilled to obtain 1.8 g (yield: 53.0%) of 1,1,3,3,5,5-hexachloro-1,3,5-trisilacyclohexane, 1.0 g (yield: 17.3%) of 1,1,1,3,3,5,5,5-octachloro-1,3,5-trisilapentane, and 3.2 g (yield: 48.2%) of n-hexyltrichlorosilane were obtained.

The results of analyzing the obtained products by using 300 MHz 1H magnetic resonance showed that, in n-hexyltrichlorosilane, —$CH_2$—$CH_3$ peak was confirmed at δ0.91 ppm (m, 3H), —$(CH_2)_4$ peak was confirmed at δ1.30-1.45 (m, 8H), and $Cl_3Si$—$CH_2$ peak was confirmed at δ1.61 (m, 2H). In 1,1,3,3,5,5-hexachloro-1,3,5-trisilacyclohexane, Si—$CH_2$—Si peak was confirmed at δ1.46 ppm (s, 6H). In 1,1,1,3,3,5,5,5-octachloro-1,3,5-trisilapentane, Si—$CH_2$—C peak was confirmed at δ1.71 ppm (s, 4H).

Embodiment 14: Reaction of (chloromethyl)methyldichlorosilane and (trichlorosilylmethyl)dichlorosilane (catalyst: tetrabutylphosphonium chloride)

In the same manner as that of Embodiment 1, 4.9 g (0.030 mol) of (chloromethyl)methyldichlorosilane, 7.5 g (0.030 mol) of (trichlorosilylmethyl)dichlorosilane, and 0.9 g (0.003 mol) of tetrabutylphosphonium chloride were put in a 25 ml stainless steel tube and reacted at 150° C. for two hours. The reactant was vacuum-distilled to obtain 1.5 g (yield: 45.5%) of 1,1,3,3,5,5-hexachloro-1,3,5-trisilacyclohexane, 1.0 g (yield: 16.3%) of 1,1,1,3,3,5,5,5-octachloro-1,3,5-trisilapentane, and 2.8 g (yield: 35.4%) of 1,1,1,3,3-pentachloro-1,3-disilabutane were obtained.

The results of analyzing the obtained products by using 300 MHz 1H magnetic resonance showed that, in 1,1,1,3,3-pentachloro-1,3-disilabutane, $Cl_3Si$—$CH_3$ peak was confirmed at δ0.94 ppm (s, 3H) and Si—$CH_2$ was conformed at δ1.58 ppm (s, 2H). In 1,1,3,3,5,5-hexachloro-1,3,5-trisilacyclohexane, Si—$CH_2$—Si peak was confirmed at δ1.46 ppm (s, 6H). In 1,1,1,3,3,5,5,5-octachloro-1,3,5-trisilapentane, Si—$CH_2$—C peak was confirmed at δ1.71 ppm (s, 4H).

Embodiment 15: Reaction of allyl chloride and (trichlorosilylmethyl)dichlorosilane (catalyst: tetrabutylphosphonium chloride)

In the same manner as that of Embodiment 1, 2.3 g (0.030 mol) of allyl chloride, 7.5 g (0.030 mol) of (trichlorosilylmethyl)dichlorosilane, and 0.9 g (0.003 mol) of tetrabutylphosphonium chloride were put in a 25 ml stainless steel tube and reacted at 150° C. for two hours. The reactant was vacuum-distilled to obtain 1.8 g (yield: 54.4%) of 1,1,3,3,5,5-hexachloro-1,3,5-trisilacyclohexane, 0.7 g (yield: 12.3%) of 1,1,1,3,3,5,5,5-octachloro-1,3,5-trisilapentane, and 2.0 g (yield: 38.3%) of allyltrichlorosilane were obtained.

The results of analyzing the obtained products by using 300 MHz 1H magnetic resonance showed that, in allyltrichlorosilane, C—$CH_2$—Si peak was confirmed at δ2.36 ppm (d, 2H), $CH_2$=peak was conformed at δ5.22 ppm (m, 2H), and CH=peak was confirmed at δ5.80 ppm (m, 1H). In 1,1,3,3,5,5-hexachloro-1,3,5-trisilacyclohexane, Si—$CH_2$—Si peak was confirmed at δ1.46 ppm (s, 6H). In 1,1,1,3,3,5,5,5-octachloro-1,3,5-trisilapentane, Si—$CH_2$—C peak was confirmed at δ1.71 ppm (s, 4H).

Embodiment 16: Reaction of 4-chlorobenzylchloride and (trichlorosilylmethyl)dichlorosilane (catalyst: tetrabutylphosphonium chloride)

In the same manner as that of Embodiment 1, 5.3 g (0.030 mol) of 4-chlorobenzylchloride, 7.5 g (0.030 mol) of (trichlorosilylmethyl)dichlorosilane, and 0.9 g (0.003 mol) of tetrabutylphosphonium chloride were put in a 25 ml stainless steel tube and reacted at 130° C. for four hours. The reactant was vacuum-distilled to obtain 1.8 g (yield: 52.8%) of 1,1,3,3,5,5-hexachloro-1,3,5-trisilacyclohexane, 0.7 g (yield: 12.3%) of 1,1,1,3,3,5,5,5-octachloro-1,3,5-trisilapentane, and 3.3 g (yield: 42.3%) of (4-chlorobenzyl)trichlorosilane were obtained.

The results of analyzing the obtained products by using 300 MHz 1H magnetic resonance showed that, in (4-chlorobenzyl)trichlorosilane, C—$CH_2$—Si peak was confirmed at δ2.93 ppm (s, 2H) and Ar—H peak was conformed at δ7.37 ppm (m, 4H). In 1,1,3,3,5,5-hexachloro-1,3,5-trisilacyclohexane, Si—$CH_2$—Si peak was confirmed at δ1.46 ppm (s, 6H). In 1,1,1,3,3,5,5,5-octachloro-1,3,5-trisilapentane, Si—$CH_2$—C peak was confirmed at δ1.71 ppm (s, 4H).

Embodiment 17: Reaction of isopropylchloride and (trichlorosilylmethyl)dichlorosilane (catalyst: tetrabutylphosphonium chloride)

In the same manner as that of Embodiment 1, 2.4 g (0.030 mol) of isopropylchloride, 7.5 g (0.030 mol) of (trichlorosilylmethyl)dichlorosilane, and 0.9 g (0.003 mol) of tetrabutylphosphonium chloride were put in a 25 ml stainless steel tube and reacted at 180° C. for thirteen hours. The reactant was vacuum-distilled to obtain 1.4 g (yield: 42.4%) of 1,1,3,3,5,5-hexachloro-1,3,5-trisilacyclohexane, 1.0 g (yield: 16.3%) of 1,1,1,3,3,5,5,5-octachloro-1,3,5-trisilapentane, and 1.8 g (yield: 33.3%) of isopropyltrichlorosilane were obtained.

The results of analyzing the obtained products by using 300 MHz 1H magnetic resonance showed that, in isopropyltrichlorosilane, CH—(CH$_3$)$_2$ peak was confirmed at δ1.18 ppm (d, 6H) and Si—CH—(CH$_3$)$_2$ peak was confirmed at δ1.52 ppm (m, 1H). In 1,1,3,3,5,5-hexachloro-1,3,5-trisilacyclohexane, Si—CH$_2$—Si peak was confirmed at δ1.46 ppm (s, 6H). In 1,1,1,3,3,5,5,5-octachloro-1,3,5-trisilapentane, Si—CH$_2$—C peak was confirmed at δ1.71 ppm (s, 4H).

Embodiment 18: Reaction of 1-3-dichloropropane and (trichlorosilylmethyl)dichlorosilane (catalyst: tetrabutylphosphonium chloride)

In the same manner as that of Embodiment 1, 1.7 g (0.015 mol) of 1,3-dichloropropane, 7.5 g (0.030 mol) of (trichlorosilylmethyl)dichlorosilane, and 0.9 g (0.003 mol) of tetrabutylphosphonium chloride were put in a 25 ml stainless steel tube and reacted at 150° C. for ten hours. The reactant was vacuum-distilled to obtain 1.6 g (yield: 47.2%) of 1,1,3,3,5,5-hexachloro-1,3,5-trisilacyclohexane, 0.7 g (yield: 11.8%) of 1,1,1,3,3,5,5,5-octachloro-1,3,5-trisilapentane, 2.5 g (yield: 54.2%) of bis(trichlorosilyl)propane, and 0.4 g (yield: 12.2%) of 3-(chloropropyl)trichlorosilane were obtained.

The results of analyzing the obtained products by using 300 MHz 1H magnetic resonance showed that, in 1.3-bis (trichlorosilyl)propane, Si—CH$_2$— peak was confirmed at δ1.56 ppm (m, 4H) and C—CH$_2$—C peak was confirmed at δ1.92 ppm (m, 2H). In 3-(chloropropyl)trichlorosilane, Si—CH$_2$ peak was confirmed at δ1.58 ppm (m, 2H), C—CH$_2$—C peak was confirmed at δ2.06 ppm (m, 2H), and CH$_2$Cl peak was confirmed at δ3.61 ppm (t, 2H). In 1,1,3,3,5,5-hexachloro-1,3,5-trisilacyclohexane, Si—CH$_2$—Si peak was confirmed at δ1.46 ppm (m, 4H). In 1,1,1,3,3,5,5,5-octachloro-1,3,5-trisilapentane, Si—CH$_2$—C peak was confirmed at δ1.71 ppm (s, 4H).

Embodiment 19: Reaction of 4-methoxybenzylchloride and (trichlorosilylmethyl)dichlorosilane (catalyst: tetrabutylphosphonium chloride)

In the same manner as that of Embodiment 1, 4.7 g (0.030 mol) of 4-methoxybenzylchloride, 7.5 g (0.030 mol) of (trichlorosilylmethyl)dichlorosilane, and 0.9 g (0.003 mol) of tetrabutylphosphonium chloride were put in a 25 ml stainless steel tube and reacted at 150° C. for four hours. The reactant was vacuum-distilled to obtain 1.9 g (yield: 54.7%) of 1,1,3,3,5,5-hexachloro-1,3,5-trisilacyclohexane, 0.64 g (yield: 10.8%) of 1,1,1,3,3,5,5,5-octachloro-1,3,5-trisilapentane, 3.3 g (yield: 42.4%) of (4-methoxybenzyl)trichlorosilane were obtained.

The results of analyzing the obtained products by using 300 MHz 1H magnetic resonance showed that, in (4-methoxybenzyl)trichlorosilane, Si—CH$_2$—C peak was confirmed at δ2.88 ppm (s, 2H), —O—CH$_3$ was confirmed at δ3.83 ppm, and Ar—H peak was confirmed at δ7.15 ppm (d, 2H) and δ6.90 ppm (d, 2H). In 1,1,3,3,5,5-hexachloro-1,3,5-trisilacyclohexane, Si—CH$_2$—Si peak was confirmed at δ1.46 ppm (s, 6H). In 1,1,1,3,3,5,5,5-octachloro-1,3,5-trisilapentane, Si—CH$_2$—C peak was confirmed at δ1.71 ppm (s, 4H).

What is claimed is:

1. A method for preparing cyclic trisilaalkane represented by Chemical Formula 2 or a linear trisilaalkane represented by Chemical Formula 3 by reacting bischlorosilylmethane having an Si—H bond represented by Chemical Formula 1 shown below alone under the presence of a quaternary organic phosphonium salt catalyst:

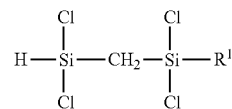

[Chemical Formula 1]

wherein R$^1$ is hydrogen, a halogen atom, or an alkyl group,

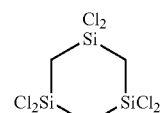

[Chemical Formula 2]

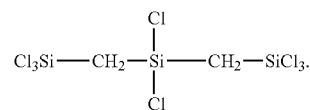

[Chemical Formula 3]

2. The method of claim 1, wherein the quaternary organic phosphonium salt catalyst is represented by Chemical Formulas 4a and 4b shown below:

[Chemical Formula 4a]

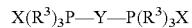

[Chemical Formula 4b]

wherein X is a halogen atom, R$^3$, which is the same or different, indicates an alkyl group of C$_1$~C$_{12}$ or —(CH$_2$)$_n$—C$_6$H$_5$ (here, n is 0 or 1~6), two R$^3$s can be covalently bonded to form 4-atom rings or 8-atom rings, and Y is an alkylene group of C$_1$~C$_{12}$.

3. The method of claim 1, wherein the quaternary organic phosphonium salt catalyst is immobilized in one or more carriers selected from the group constituting of a silicon resin, silica, inorganic complexing agent, and an organic polymer.

4. The method of claim 1, wherein the quaternary organic phosphonium salt catalyst is included within the range of 0.05 mol to 0.5 mol with respect to 1 mol of bischlorosilylmethane having the Si—H bond represented by Chemical Formula 1.

5. The method of claim 1, wherein the reaction is performed within a temperature range of 10° C. to 250° C.

6. The method of claim 1, wherein the reaction is performed without a reaction solvent or under the presence of an aromatic hydrocarbon solvent.

7. The method of claim 1, wherein an organic chloride represented by Chemical Formula 5 shown below is further contained as a reactant:

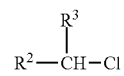

[Chemical Formula 5]

wherein R$^2$ is selected from among a halogen atom; a linear or cyclic alkyl group having 1 to 6 carbons; a silane derivative residue selected from the group consisting of —SiCl$_3$, —SiMeCl$_2$, —SiHCl$_2$, —SiMe$_2$Cl, and —SiMe$_3$; an alkene group having 2 to 5 carbons containing an unsaturated bond; an aromatic group represented as —Ar(R')q (here, Ar is aromatic hydrocarbon having 6 to 14 carbons, R' is an alkyl group, halogen, an alkoxy group, or a vinyl group, each having 1 to 4 carbons, and q is an integer of 0 to 5); an alkyl chloride group represented as —(CH$_2$)pCl (here, p is an integer of 1 to 9); or methyl chloride aromatic group represented as —Ar(CH$_2$)Cl (here, Ar is aromatic group hydrocarbon having 6 to 14 carbons), and R$^3$ is selected from among a hydrogen atom; a halogen atom; a linear or cyclic alkyl group having 1 to 6 carbons; and an aromatic group represented as —Ar(R')q (here, Ar is aromatic hydrocarbon having 6 to 14 carbons, R' is an alkyl group, halogen, an alkoxy group, or a vinyl group, each having 1 to 4 carbons, and q is an integer of 0 to 5).

8. The method of claim 7, wherein an organic trichlorosilane derivative represented by Chemical Formula 6 shown below is further obtained:

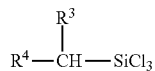

[Chemical Formula 6]

wherein R$^3$ is selected from among a hydrogen atom; a linear or cyclic alkyl group having 1 to 6 carbons; or an aromatic group represented as —Ar(R')q (here, Ar is aromatic hydrocarbon having 6 to 14 carbons, R' is an alkyl group, halogen, an alkoxy group, or a vinyl group, each having 1 to 4 carbons, and q is an integer of 0 to 5), and R$^4$ is selected from among a linear or cyclic alkyl group having 1 to 6 carbons; a silane derivative residue selected from the group consisting of —SiCl$_3$, —SiMeCl$_2$, —SiHCl$_2$, —SiMe$_2$Cl, and —SiMe$_3$; an alkene group having 2 to 5 carbons containing an unsaturated bond; or an aromatic group represented as —Ar(R')q (here, Ar is aromatic hydrocarbon having 6 to 14 carbons, R' is an alkyl group, halogen, an alkoxy group, or a vinyl group, each having 1 to 4 carbons, and q is an integer of 0 to 5), wherein when R$^2$ in Chemical Formula 5 is —(CH$_2$)pCl, —Ar(CH$_2$)Cl, R$^4$ in Chemical Formula 6 is —(CH$_2$)pSiCl$_3$, —Ar(CH$_2$)SiCl$_3$.

9. The method of claim 7, wherein the organic chloride represented by Chemical Formula 5 is reacted within the range of 0.5 mol to 8 mol with respect to 1 mol of bischlorosilylmethane having the Si—H bond represented by Chemical Formula 1.

* * * * *